(12) United States Patent
Kurokawa et al.

(10) Patent No.: US 11,883,954 B2
(45) Date of Patent: Jan. 30, 2024

(54) FLEXIBLE MEMBER

(71) Applicant: NHK SPRING CO., LTD., Kanagawa (JP)

(72) Inventors: Shimpei Kurokawa, Kanagawa (JP); Yosuke Kawai, Kanagawa (JP)

(73) Assignee: NHK SPRING CO., LTD., Kanagawa (JP)

( * ) Notice: Subject to any disclaimer, the term of this patent is extended or adjusted under 35 U.S.C. 154(b) by 295 days.

(21) Appl. No.: 17/601,711

(22) PCT Filed: Apr. 13, 2020

(86) PCT No.: PCT/JP2020/016305
§ 371 (c)(1),
(2) Date: Oct. 6, 2021

(87) PCT Pub. No.: WO2020/209387
PCT Pub. Date: Oct. 15, 2020

(65) Prior Publication Data
US 2022/0193933 A1    Jun. 23, 2022

(30) Foreign Application Priority Data
Apr. 11, 2019 (JP) .................. 2019-075949

(51) Int. Cl.
*B25J 18/06* (2006.01)
*A61B 34/30* (2016.01)
*F16F 1/32* (2006.01)

(52) U.S. Cl.
CPC .............. *B25J 18/06* (2013.01); *A61B 34/30* (2016.02); *F16F 1/328* (2013.01); *F16F 2226/04* (2013.01)

(58) Field of Classification Search
CPC ............................ F16F 1/328; F16F 2226/048
See application file for complete search history.

(56) References Cited

U.S. PATENT DOCUMENTS 4,901,987 A * 2/1990 Greenhill .................. F16F 1/06
267/182
5,072,917 A * 12/1991 Pleva ........................ F16F 1/32
411/162

(Continued)

FOREIGN PATENT DOCUMENTS

| JP | H04296260 | 10/1992 |
|---|---|---|
| JP | H0567836 | 9/1993 |

(Continued)

OTHER PUBLICATIONS

"Search Report of Europe Counterpart Application", dated May 30, 2022, pp. 1-6.

(Continued)

*Primary Examiner* — Jake Cook
(74) *Attorney, Agent, or Firm* — JCIPRNET

(57) ABSTRACT

A flexible member is provided which can have excellent load resistance and flexibility while being more compact. This flexible member has a main body part in which multiple wave washers having closed ring shapes is stacked in an axial direction and joined to each other by multiple joint parts, and the main body part is able to be bent with respect to the axial direction due to elastic deformation of the wave washers. Each of the joint parts includes: a pair of welded parts in linear shape, being gradually separated from each other in a circumferential direction from an inner circumferential side toward an outer circumferential side of the wave washer.

10 Claims, 10 Drawing Sheets

(56) References Cited

U.S. PATENT DOCUMENTS

| | | | |
|---|---|---|---|
| 5,558,393 A | 9/1996 | Hawkins et al. | |
| 7,210,181 B1 * | 5/2007 | Price | A47C 27/065 |
| | | | 5/255 |
| 2003/0222385 A1 * | 12/2003 | Cai | F16F 1/328 |
| | | | 267/162 |
| 2013/0312564 A1 | 11/2013 | Kim et al. | |
| 2014/0371764 A1 | 12/2014 | Oyola et al. | |
| 2016/0235274 A1 * | 8/2016 | Graham | A01K 85/005 |
| 2018/0370045 A1 | 12/2018 | Kan | |

FOREIGN PATENT DOCUMENTS

| | | |
|---|---|---|
| JP | 2014038075 | 2/2014 |
| JP | 2016075390 | 5/2016 |

OTHER PUBLICATIONS

"International Search Report (Form PCT/ISA/210) of PCT/JP2020/016305," dated Jul. 7, 2020, with English translation thereof, pp. 1-4.

* cited by examiner (A) (B)

FLEXIBLE MEMBER

CROSS-REFERENCE TO RELATED APPLICATION

This application is a 371 application of the international PCT application serial no. PCT/JP2020/016305, filed on Apr. 13, 2020, which claims the priority benefit of Japan application no. 2019-075949, filed on Apr. 11, 2019. The entirety of the above—mentioned patent applications is hereby incorporated by reference herein and made a part of this specification.

TECHNICAL FIELD

The present invention relates to a flexible member provided for a joint functioning part of a robot or the like.

BACKGROUND ART

Some robots, manipulators, actuators, and the like in various fields have a joint functioning part capable of performing bending operation using a flexible member. Regarding a flexible member used in such a joint functioning part, Japanese Patent Laid-Open No. 2014-38075 discloses a coil spring.

A coil spring can secure a high degree of freedom with respect to bending operation of a joint functioning part. However, there has been a limit to reduction in size of a coil spring due to the need to secure load resistance and flexibility.

SUMMARY OF INVENTION

Technical Problem

A problem to be solved is that there is a limit in securing load resistance and flexibility while achieving reduction in size.

Solution to Problem

The present invention provides a flexible member which can have excellent load resistance and flexibility while achieving reduction in size. This flexible member includes: a main body part in which a plurality of wave washers having closed ring shapes is stacked in an axial direction and joined to each other by a plurality of joint parts, and the main body part is able to be bent with respect to the axial direction due to elastic deformation of the wave washers. Each of the plurality of joint parts includes: a pair of welded parts in linear shape, being gradually separated from each other in a circumferential direction from an inner circumferential side toward an outer circumferential side of the wave washer.

Advantageous Effects of Invention

According to the present invention, the main body part of the flexible member can be bent due to deformation of the plurality of wave washers. Therefore, it is possible to obtain a flexible member having excellent load resistance and flexibility while achieving reduction in size.

Furthermore, in the present invention, occurrence of a difference between the deformation amounts in the inner and outer circumferences when the wave washers are deformed can be curbed by the pair of welded parts, and deviation in stress acting on portions around the joint parts can be curbed. As a result, the present invention can improve durability of a flexible member.

DESCRIPTION OF EMBODIMENT

An objective of obtaining a flexible member which can have excellent load resistance and flexibility while achieving reduction in size is realized while durability is improved.

That is, a flexible member includes a main body part in which a plurality of wave washers having closed ring shapes is stacked in an axial direction and joined to each other by a plurality of joint parts and which is able to be bent with respect to the axial direction due to elastic deformation of the wave washers. Each of the plurality of joint parts includes: a pair of welded parts in linear shape, being gradually separated from each other in a circumferential direction from an inner circumferential side toward an outer circumferential side of the wave washer.

In the constitution, in the pair of welded parts, one welded part may be provided on a second line extending in a direction intersecting a first line extending in a radiating direction from a center of the wave washer, and the other welded part may be provided on a third line extending in a direction intersecting the second line.

In the constitution, each of the pair of welded parts may be provided to have a continuously linear shape.

The pair of welded parts may have a V-shape in which the welded parts overlap each other on the inner circumferential side in the wave washer.

In the constitution, each of the plurality of wave washers may include a plurality of mountain parts and valley parts between the mountain parts in the circumferential direction, the mountain parts and the valley parts of adjacent wave washers may abut each other, and abutment portions of the mountain parts and the valley parts may be joined to each other by the joint parts.

Example 1

[Structure of Manipulator]

Figure 1:
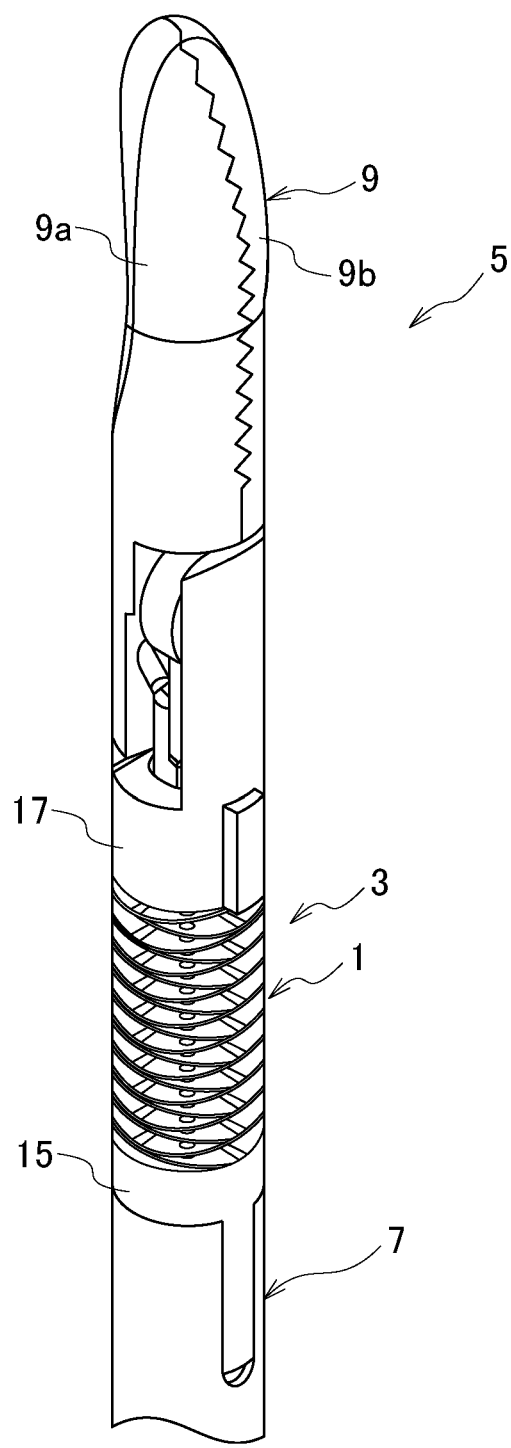
FIG. 1 is a perspective view illustrating a manipulator using a flexible member according to an Example 1 of the present invention.
Figure 2:
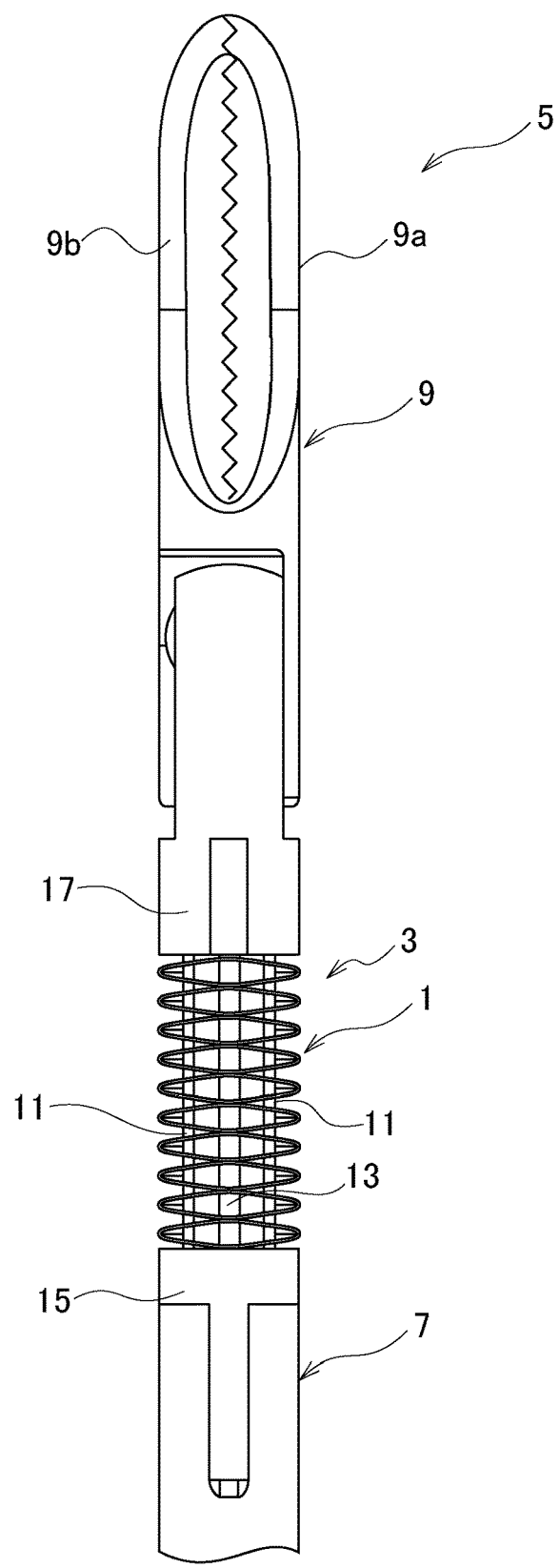
FIG. 2 is a front view illustrating the manipulator in FIG. 1.
Figure 3:
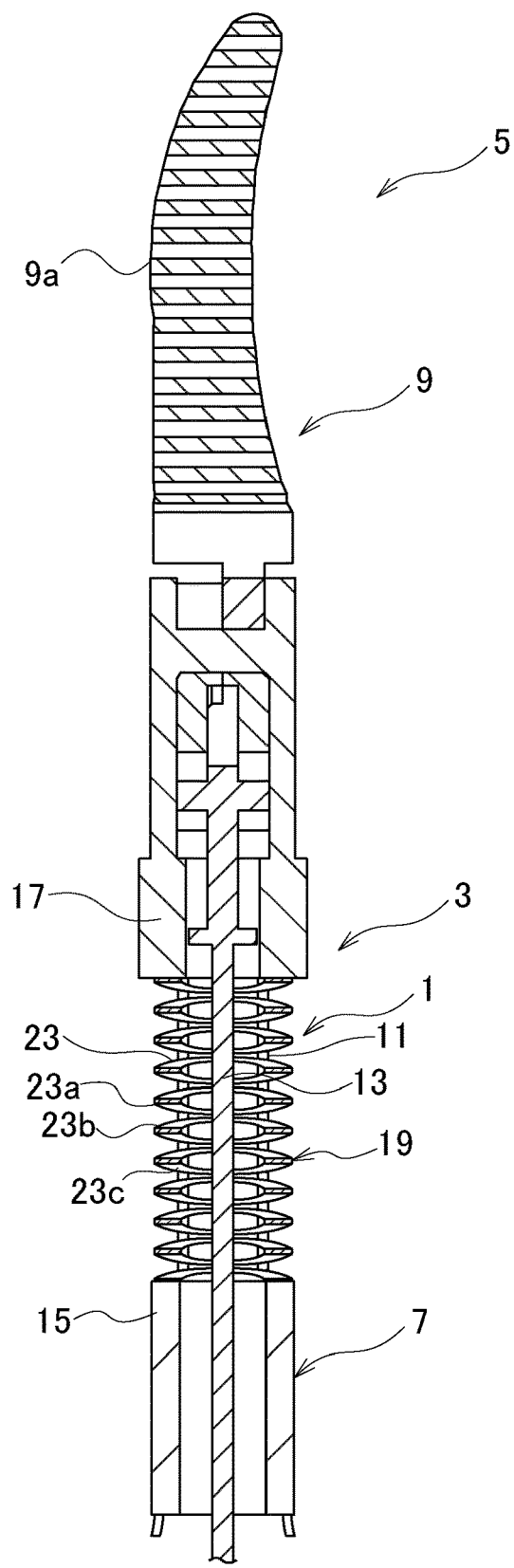
FIG. 3 is a cross-sectional view of the manipulator in FIG. 1.

FIG. 1 is a perspective view illustrating a manipulator using a flexible member according to an Example 1 of the present invention, FIG. 2 is a front view of the same, and FIG. 3 is a cross-sectional view of the same.

The present example will be described regarding a medical manipulator 5 as an example of a robot, a manipulator, or an actuator which has a joint functioning part 3 using a flexible member 1.

The manipulator 5 constitutes a tip of a robot arm of a surgical robot and is operated by a doctor or the like. The manipulator 5 may be a manual manipulator which is directly operated by a doctor or the like without being attached to a surgical robot. In addition, a robot, a manipulator, or an actuator in which the flexible member 1 can be applied is not limited to the manipulator 5, and the flexible member 1 may be adopted in other fields such as industrial robots.

The manipulator 5 includes a shaft part 7, the joint functioning part 3, and an end effector 9.

The shaft part 7 is formed to have a hollow tubular shape, for example, a cylindrical shape. Driving wires 11 for driving the joint functioning part 3 or a push-pull cable 13 for driving the end effector 9 passes through the inside of the shaft part 7. The end effector 9 is provided at a tip of the shaft part 7 with the joint functioning part 3 therebetween.

The joint functioning part 3 performs bending operation with respect to an axial direction in response to an operation of the driving wires 11. The axial direction denotes a direction along an axial center of the flexible member 1, which will be described below. However, there is no need for the axial direction to be a direction strictly parallel to the axial center. Therefore, the axial direction also includes a direction slightly inclined with respect to the axial center. Details of the joint functioning part 3 will be described below.

The end effector 9 is an instrument which is attached to a movable part 17 of the joint functioning part 3 and performs operation according to a purpose. The end effector 9 of the present example is a forceps and includes a pair of clasping parts 9a and 9b. This end effector 9 can be directed in a desired direction in response to bending operation of the joint functioning part 3. In addition, the pair of clasping parts 9a and 9b can be opened and closed in response to an operation of the push-pull cable 13.

The end effector 9 is not limited to a forceps, for example, it can be scissors, a clasping retractor, a needle driver, a camera, or the like.

[Structure of Joint Functioning Part]

Figure 4:
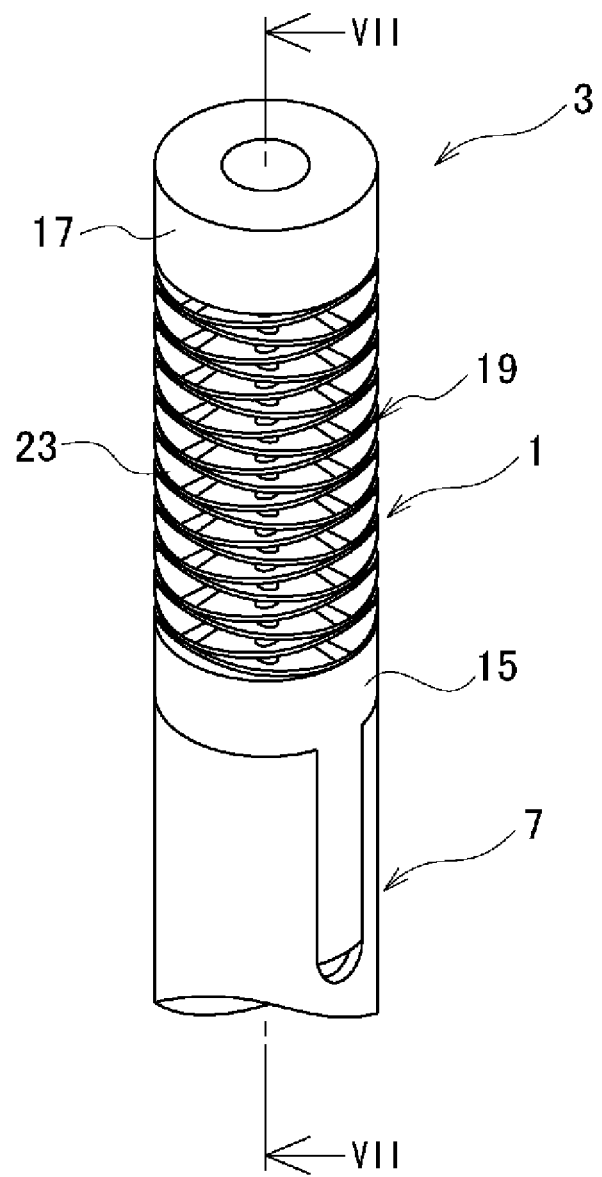
FIG. 4 is a perspective view mainly illustrating a joint functioning part in which a part of the manipulator in FIG. 1 is omitted.
Figure 5:
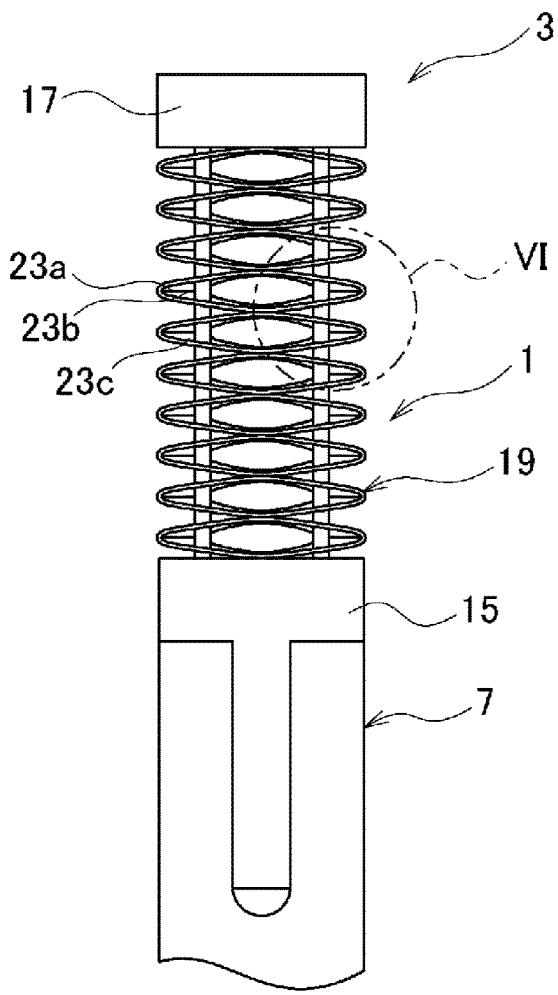
FIG. 5 is a side view mainly illustrating the joint functioning part in FIG. 4.
Figure 6:
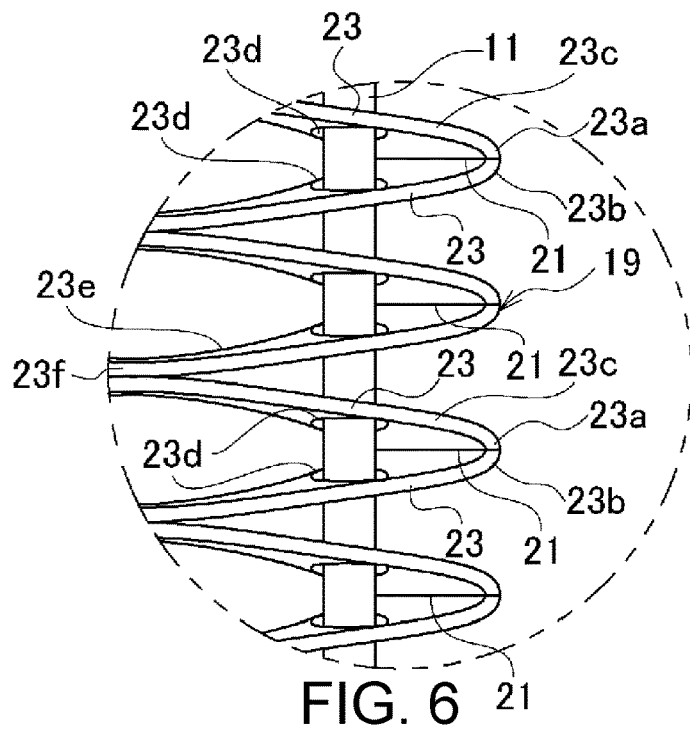
FIG. 6 is an enlarged view of the VI part in FIG. 5.
Figure 7:
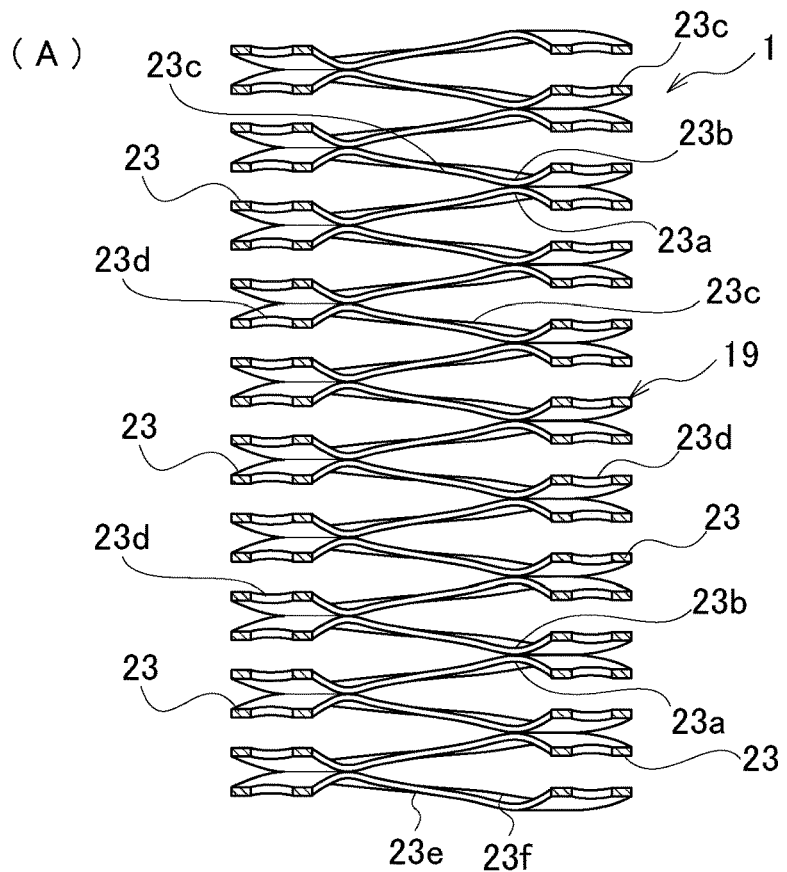
In FIGS. 7, (A) and (B) are cross-sectional views illustrating a flexible member of the joint functioning part along line VII-VII in FIG. 4, in which (A) of FIG. 7 illustrates the flexible member at a normal time, and (B) of FIG. 7 illustrates the flexible member at the time of being bent.
Figure 7:
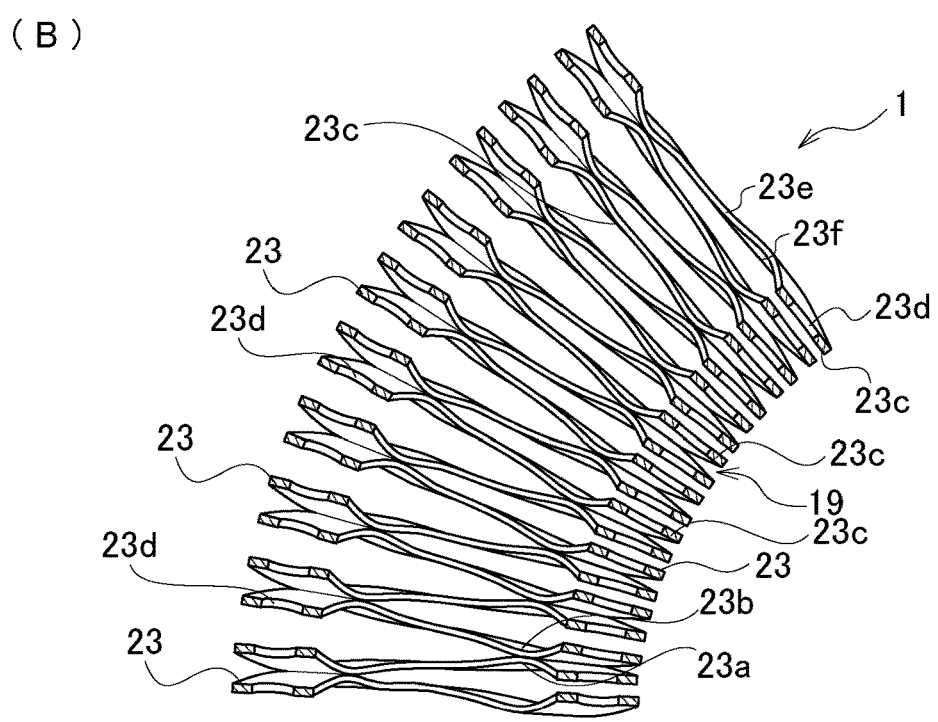

FIG. 4 is a perspective view mainly illustrating the joint functioning part 3 in which a part of the manipulator 5 in FIG. 1 is omitted. FIG. 5 is a side view of the same. FIG. 6 is an enlarged view of the VI part in FIG. 5. In FIGS. 7, (A) and (B) are cross-sectional views illustrating the flexible member 1 of the joint functioning part 3 along line VII-VII in FIG. 4, in which (A) of FIG. 7 illustrates the flexible member 1 at a normal time, and (B) of FIG. 7 illustrates the flexible member 1 at the time of being bent.

As in FIG. 1 to (B) of FIG. 7, the joint functioning part 3 includes a base part 15, the movable part 17, and the flexible member 1.

The base part 15 is formed of a metal or the like to have a columnar shape and is attached to the tip of the shaft part 7. The push-pull cable 13 is inserted through an axial center part of the base part 15 in the axial direction. Around the push-pull cable 13, the driving wires 11 are inserted through the base part 15 in the axial direction.

The movable part 17 is formed of a metal or the like to have a columnar shape and is attached to the end effector 9. An axial center part of the movable part 17 is inserted through the push-pull cable 13. A tip of the push-pull cable 13 is linked to the end effector 9.

This movable part 17 is supported by the base part 15 with the flexible member 1 therebetween. Tip parts of the driving wires 11 are fixed to the movable part 17. For this reason, the movable part 17 is deformed with respect to the base part 15 due to an operation of the driving wires 11 and can direct the end effector 9 in a desired direction.

The flexible member 1 enables the joint functioning part 3 to perform bending operation. The flexible member 1 is interposed between the base part 15 and the movable part 17. The flexible member 1 is bent in response to deformation of the movable part 17 with respect to the base part 15. The driving wires 11 and the push-pull cable 13 pass through the flexible member 1 in the axial direction.

In the flexible member 1, both end parts of a main body part 19 are fixed to the base part 15 and the movable part 17, respectively. This fixing can be performed using joint parts 21 (which will be described below) or a different fixing devices.

The main body part 19 has a plurality of wave washers 23. The wave washers 23 are stacked in the axial direction, and wave washers 23 adjacent to each other in the axial direction are joined to each other. The main body part 19 can be bent due to elastic deformation of the wave washers 23.

Each of the wave washers 23 is a plate member formed of a metal or the like to have having closed ring shapes. The wave washers 23 of the present example are plate members formed of stainless steels to have toric shapes. A width of the wave washer 23 between inner and outer circumferences 23e and 23f in a radial direction and a plate thickness thereof are uniform in a circumferential direction. However, the widths and the plate thicknesses of the wave washers 23 may not be uniform in the circumferential direction.

Each of the wave washers 23 has a plurality of mountain parts 23a and valley parts 23b in the circumferential direction. Each of the valley parts 23b is provided between mountain parts 23a adjacent to each other in the circumferential direction. Each of the wave washers 23 of the present example has two mountain parts 23a facing each other in the radial direction and has two valley parts 23b facing each other in the radial direction between the mountain parts 23a. Therefore, in the present example, the mountain parts 23a and the valley parts 23b are alternately provided at intervals of 90 degrees in the circumferential direction.

The mountain parts 23a and the valley parts 23b lie from the inner circumference 23e to the outer circumference 23f of the wave washer 23. The mountain parts 23a and the valley parts 23b are formed to be curved in arc shapes in a direction opposite to the axial direction. In wave washers 23 adjacent to each other in the axial direction, the mountain parts 23a of the wave washer 23 on one side abut the valley parts 23b of the wave washer on the other side. Due to expansion and contraction of the mountain parts 23a and the valley parts 23b, each of the wave washers 23 can be deformed due to elastic expansion and contraction in the axial direction.

Regarding the mountain parts 23a and the valley parts 23b abutting each other, abutment portions of both the parts are joined to each other by the joint parts 21. Accordingly, the stacked state of the main body part 19 of the flexible member 1 is retained. Details of the joint parts 21 will be described below.

In each of the wave washers 23, the mountain parts 23a and the valley parts 23b are connected to each other through inclined parts 23c. The inclined parts 23c are inclined in the circumferential direction and have slightly twisted shapes between the inner circumference 23e and the outer circumference 23f.

Insertion holes 23d serving as through parts through which the driving wires 11 pass are provided in the inclined parts 23c. As a result, a plurality of insertion holes 23d is provided in the circumferential direction of the main body part 19. In the present example, four driving wires 11 are individually provided at intervals of 90 degrees in the circumferential direction. Therefore, in accordance with this, four insertion holes 23d are individually provided at intervals of 90 degrees in the circumferential direction in each of the wave washers 23.

The insertion holes 23d communicate with each other in the axial direction between the inclined parts 23c of wave washers 23 adjacent to each other in the axial direction. The driving wires 11 are inserted through the insertion holes 23d communicating with each other. Due to this insertion, the flexible member 1 functions as a through part through which the driving wires 11 pass in the axial direction and as a guide retaining the driving wires 11 at a predetermined position.

The insertion holes 23d have substantially circular shapes and have diameters larger than the diameters of the driving wires 11. The difference between the diameters allows inclination and deformation of the inclined parts 23c. The shapes of the insertion holes 23d are not limited to circular shapes and may have different shapes such as rectangular shapes.

The shapes, the materials, and the like of the wave washers 23 can be suitably changed in accordance with characteristics or the like required for the flexible member 1. The number and the radii of curvature of the mountain parts 23a and the valley parts 23b, the inclination angles of the inclined parts 23c, and the like can also be suitably changed in accordance with characteristics or the like required for the flexible member 1.

[Joint Part]

Figure 8:
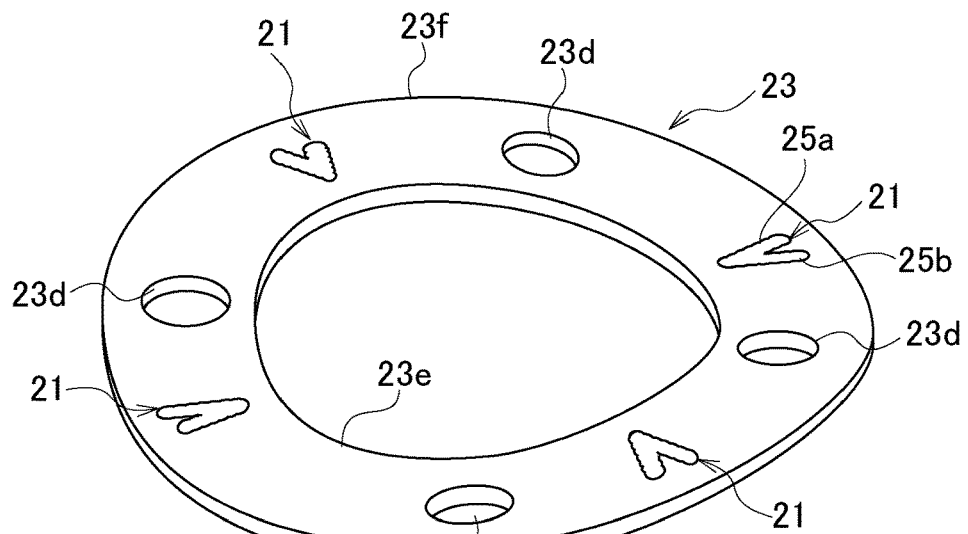
FIG. 8 is a perspective view illustrating a wave washer having joint parts.
Figure 9:
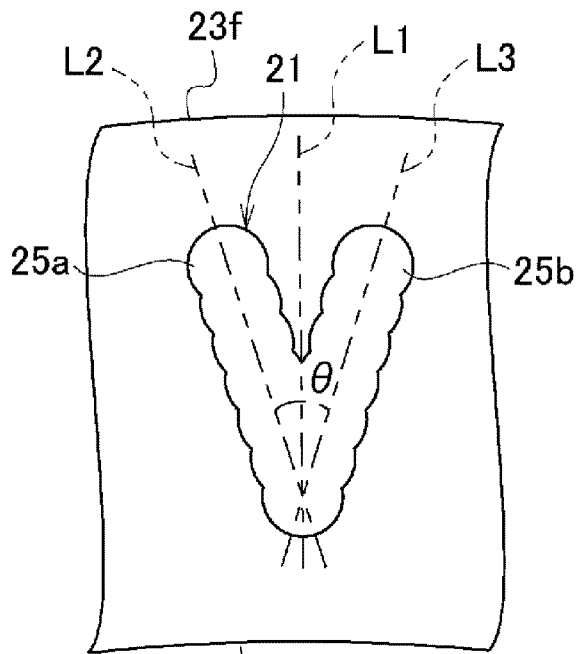
FIG. 9 is an enlarged plan view illustrating the joint part in FIG. 8.
Figure 10:
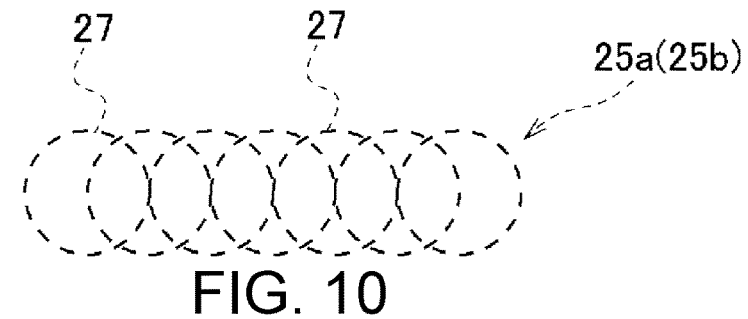
FIG. 10 is a plan view conceptually illustrating welding spots of a welded part of a joint part.

FIG. 8 is a perspective view illustrating a wave washer having the joint parts 21. FIG. 9 is an enlarged plan view of the joint part 21 in FIG. 8. FIG. 10 is a plan view conceptually illustrating welding spots 27 of a welded part 25a or 25b of the joint part 21.

The joint parts 21 are disposed at equal intervals in the circumferential direction of the wave washer 23. In the present example, the joint parts 21 are disposed at intervals of 90 degrees in each of the wave washers 23.

Each of the joint parts 21 includes: a pair of welded parts 25a and 25b in linear shape. The pair of welded parts 25a and 25b are gradually separated from each other in the circumferential direction from the inner circumference 23e side toward the outer circumference 23f side of the wave washer 23. Accordingly, the joint parts 21 curb occurrence of a difference between the deformation amounts in the inner circumference 23e and the outer circumference 23f of the wave washer 23 when the main body part 19 of the flexible member 1 is bent.

In the present example, the pair of welded parts 25a and 25b is individually formed to have continuously linear shapes and forms a V-shape in which they overlap each other on the inner circumference 23e side of the wave washer.

Specifically, the welded parts 25a and 25b are formed by spot welding. The welded parts 25a and 25b have continuously linear shapes by adjacent welding spots 27 which overlap each other or come into contact with each other in a plan view. In the present example, adjacent welding spots 27 overlap each other.

In the pair of welded parts 25a and 25b, the welded part 25a on one side is formed on a second line L2, and the welded part 25b on the other side is formed on a third line L3. The second line L2 extends in a direction intersecting a first line L1 extending in the radial direction (radiating direction) from the center of the wave washer 23. The third line L3 extends in a direction intersecting the second line L2.

In the present example, the second line L2 and the third line L3 are disposed symmetrically with respect to the first line L1. An angle θ between the second line L2 and the third line L3 is approximately 35 degrees. Each of the welded parts 25a and 25b is formed to have a linear shape such that the centers of the welding spots 27 are positioned on the second line L2 and the third line L3. The opening angle between the welded parts 25a and 25b is approximately 35 degrees which coincide with the angle θ formed by the second line L2 and the third line L3.

As in a modification example and the like which will be described below, the shapes of the welded parts 25a and 25b can be suitably set in accordance with a difference between deformation amounts in the inner and outer circumferences 23e and 23f of the wave washer 23.

[Bending Operation of Joint Functioning Part]

In the joint functioning part 3, when a doctor operates the manipulator 5, the flexible member 1 is bent by pulling any one of the driving wires 11. This joint functioning part 3 can be bent in all directions through 360 degrees by pulling some driving wires 11 in combination.

When bending is performed by pulling at least any one of the driving wires 11, in the flexible member 1, as in (B) of FIG. 7, the mountain parts 23a and the valley parts 23b are compressed at bending inner side portions with respect to a neutral axis and the mountain parts 23a and the valley parts 23b are extended at bending outer side portions with respect to the neutral axis.

Due to such deformation, the inclined parts 23c through which the operated driving wires 11 are inserted approach each other, and the flexible member 1 in its entirety is bent. Accordingly, the present example realizes bending operation having highly linear load characteristics of a bending angle and a load.

At the time of such bending, the joint parts 21 curb occurrence of a difference between the deformation amounts in the inner and outer circumferences 23e and 23f of each of the wave washers 23 in the flexible member 1.

Specifically, as described above, the pair of welded parts 25a and 25b of the joint part 21 are gradually separated from each other in the circumferential direction from the inner circumference 23e side toward the outer circumference 23f side. For this reason, in the outer circumference 23f of the wave washer 23, deformation in portions corresponding to portions between the welded parts 25a and 25b is curbed.

On the other hand, in the inner circumference 23e of the wave washer 23, since the welded parts 25a and 25b approach each other and they overlap each other in the present example, there is no curbing of deformation as in the outer circumference 23f.

Therefore, in each of the wave washers 23, the deformation amounts in the inner and outer circumferences 23e and 23f are adjusted, and occurrence of a difference between the deformation amounts in the inner and outer circumferences 23e and 23f of the wave washer 23 is curbed.

Accordingly, in the present example, deviation in stress acting on portions around the joint parts 21 is curbed, the largest stress is reduced, and thus durability of the flexible member 1 is improved.

[Stress Distribution]

Figure 11:
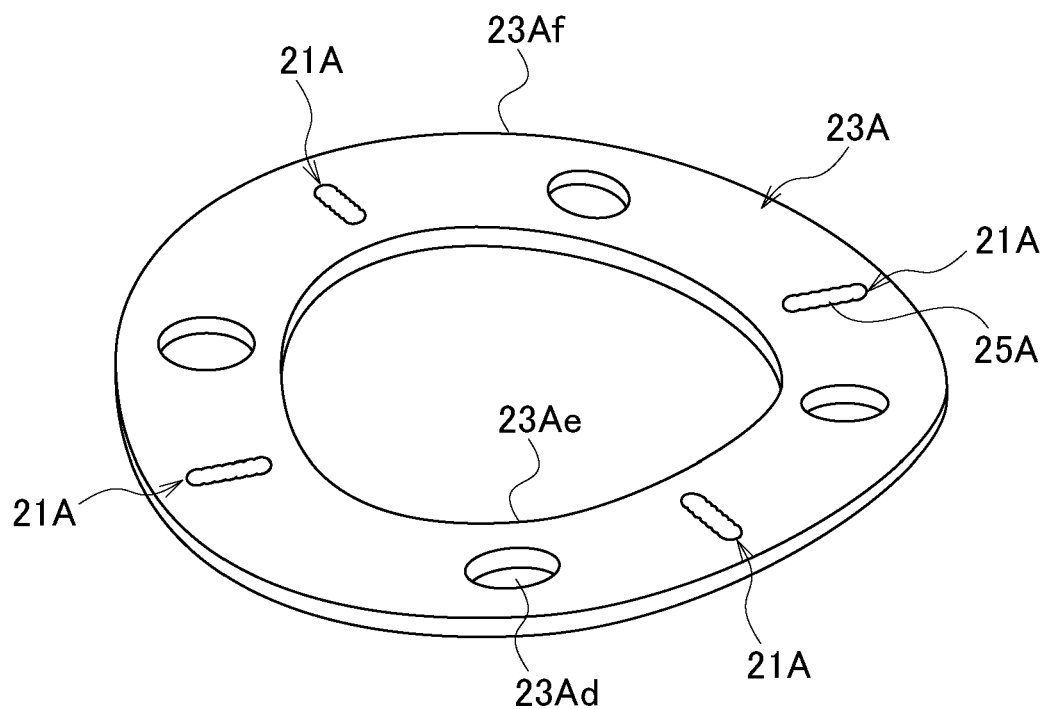
FIG. 11 is a perspective view illustrating a wave washer having joint parts according to a comparative example.
Figure 12:
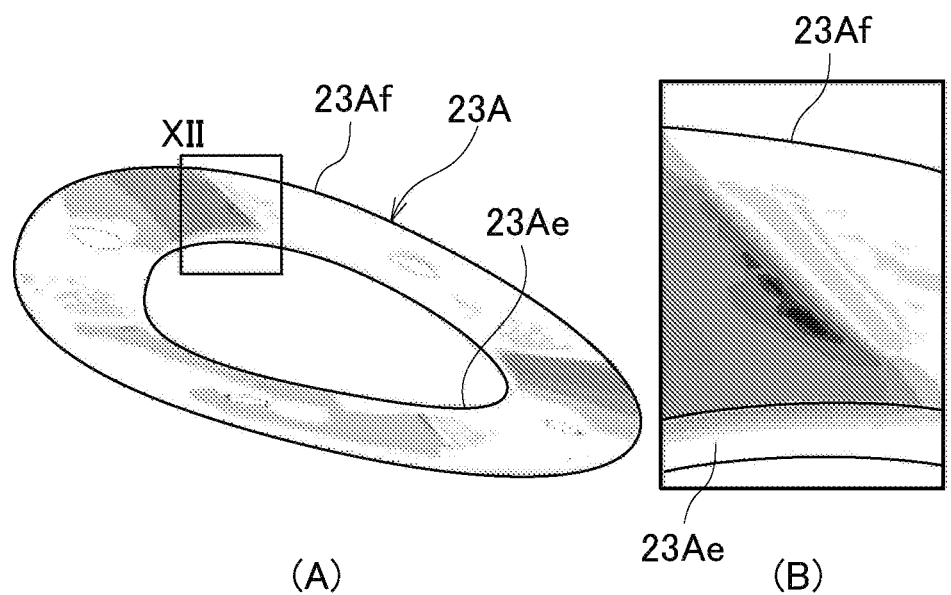
In FIGS. 12, (A) and (B) illustrate a stress distribution of the wave washer according to the comparative example in FIG. 11, in which (A) of FIG. 12 illustrates a perspective view of the wave washer in its entirety, and (B) of FIG. 12 is an enlarged view of the XII part in (A) of FIG. 12.
Figure 13:
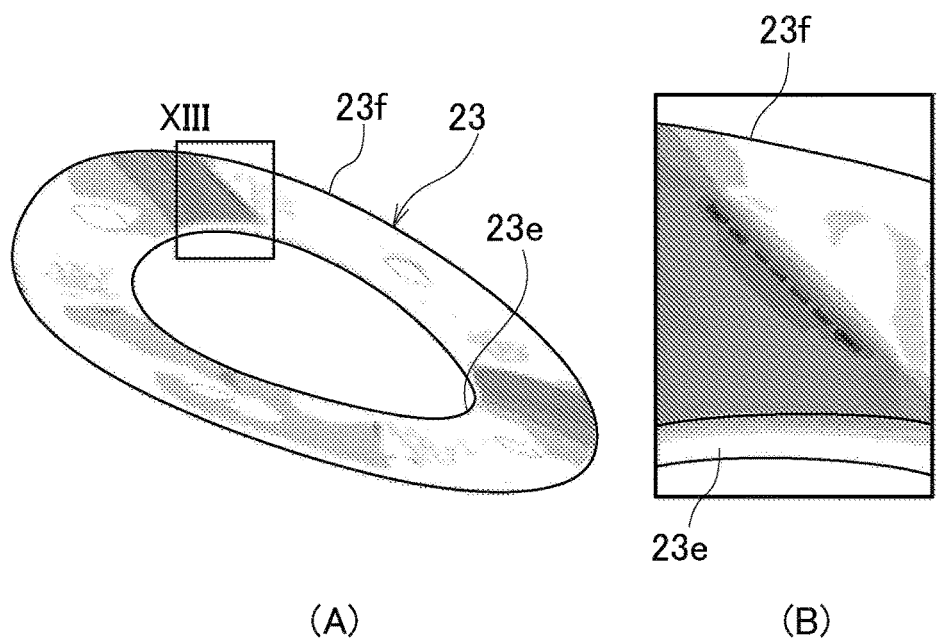
In FIGS. 13, (A) and (B) illustrate a stress distribution of the wave washer in FIG. 8, in which (A) of FIG. 13 illustrates a perspective view of the wave washer in its entirety, and (B) of FIG. 13 is an enlarged view of the XIII part in (A) of FIG. 13.

FIG. 11 is a perspective view illustrating a wave washer 23A having joint parts 21A according to a comparative example. In FIGS. 12, (A) and (B) illustrate a stress distribution of the wave washer 23A according to the comparative example, in which (A) of FIG. 12 is a perspective view of the wave washer 23A in its entirety, and (B) of FIG. 12 is an enlarged view of the XII part in (A) of FIG. 12. In FIGS. 13, (A) and (B) illustrate a stress distribution of the wave washer 23 according to the Example 1, in which (A) of FIG. 13 is a perspective view of the wave washer 23 in its entirety, and (B) of FIG. 13 is an enlarged view of the XIII part in (A) of FIG. 13.

The wave washer 23A used in a flexible member (not illustrated) of the comparative example and the wave washer 23 used in the flexible member 1 of the Example 1 were compared to each other regarding a stress distribution at the time of being bent.

The flexible member of the comparative example has a main body part in which the wave washers 23A are stacked and joined to each other in a manner similar to that in the Example 1 and has the same constitutions as the Example 1 except for the shapes of the joint parts 21A. Each of the joint parts 21A includes: a single welded part 25A formed in the radial direction in each of the wave washers 23A.

In the wave washer 23A of the comparative example, there is a difference between the deformation amounts in inner and outer circumferences 23Ae and 23Af at the time of being bent. As a result, it can be seen that portions of a high stress are locally present on the inner circumference 23Ae side in regions along the joint parts 21A. The largest stress at this time was 1,186 MPa. FIG. 12 illustrates that the darker the color, the higher the stress (the same applies to FIG. 13).

In contrast, in the wave washer 23 of the Example 1, occurrence of a difference between the deformation amounts in the inner and outer circumferences 23e and 23f at the time of being bent is curbed. For this reason, it can be seen that a stress is made uniform from the inner circumference 23e side to the outer circumference 23f side in regions along the joint parts 21. The largest stress at this time was 997 MPa, and a decrease of approximately 16% was observed in comparison with the comparative example.

In addition, in the Example 1, when the opening angle between the welded parts 25a and 25b is varied to 30 degrees, 35 degrees, and 40 degrees, the largest stress has become 1,061 MPa, 997 MPa, and 1,184 MPa, respectively.

Therefore, in the present example, it can be seen that the opening angle between the welded parts 25a and 25b is preferably set within a range of 30 degrees to 40 degrees, particularly 35 degrees.

The preferable opening angle between the welded parts 25a and 25b varies depending on the widths, the shapes, or the like of the wave washers 23.

[Effects of Example 1

As described above, the flexible member 1 of the present example includes the main body part 19 in which a plurality of wave washers 23 having closed ring shapes is stacked in the axial direction and joined to each other by a plurality of joint parts 21 and which is able to be bent with respect to the axial direction due to elastic deformation of the wave washers 23. Each of the plurality of joint parts 21 includes: a pair of welded parts 25a and 25b in linear shape which are gradually separated from each other in the circumferential direction from the inner circumference 23e toward the outer circumference 23f of the wave washer 23.

Therefore, in the present example, the linearity of load characteristics of a bending angle and a load can be enhanced, and it is possible to obtain a flexible member having excellent load resistance and flexibility while achieving reduction in size.

Furthermore, in the present example, occurrence of a difference between the deformation amounts in the inner and outer circumferences 23e and 23f when the wave washers 23 are deformed due to the pair of welded parts 25a and 25b is curbed. Therefore, in the present example, deviation in stress acting on portions around the joint parts 21 in each of the wave washers 23 is curbed so that the largest stress is reduced, and thus durability of the flexible member 1 can be improved.

In the pair of welded parts 25a and 25b, the welded part 25a on one side is formed on the second line L2 extending in a direction intersecting the first line L1 extending in the radial direction from the center of the wave washer 23, and the welded part 25b on the other side is formed on the third line L3 extending in a direction intersecting the second line L2.

For this reason, in the present example, deviation in stress acting on portions around the joint parts 21 in each of the wave washers 23 can be reliably curbed.

In addition, each of the pair of welded parts 25a and 25b is formed to have a continuously linear shape. Therefore, a stress can be made uniform along the welded parts 25a and 25b.

In addition, the pair of welded parts 25a and 25b has a V-shape in which they overlap each other on the inner circumference 23e side of the wave washer 23. Therefore, the deformation amount in the inner circumference 23e of the wave washer 23 is not carelessly curbed. For this reason, the pair of welded parts 25a and 25b can reduce adjustment of the deformation amount in the outer circumference 23f of the wave washer 23.

In addition, in the present example, bending operation can be reliably performed due to expansion and contraction of the mountain parts 23a and the valley parts 23b of the main body part 19.

Moreover, in the present example, since the mountain parts 23a and the valley parts 23b abutting each other are joined to each other, it is possible to obtain the flexible member 1 having an excellent torsional rigidity.

In addition, in the present example, the plurality of wave washers 23 has the insertion holes 23d through which the driving wires 11 are inserted. Therefore, the main body part 19 can be utilized as a guide for the driving wires 11 so that the driving wires 11 can be retained at appropriate positions, and thus more stable and accurate bending operation can be performed.

[Modification Example]

Figure 14:
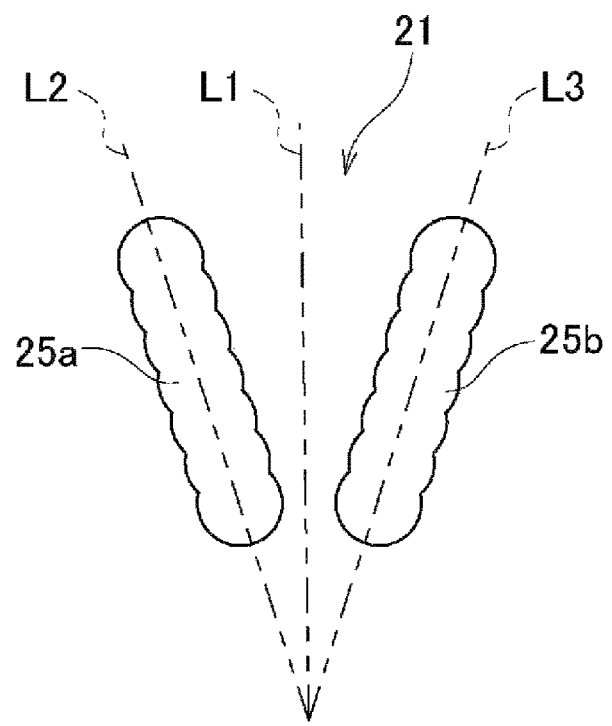
FIG. 14 is a plan view illustrating a joint part according to a modification example.
Figure 15:
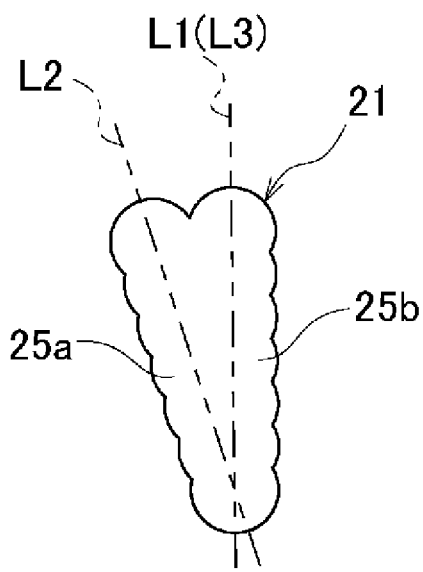
FIG. 15 is a plan view illustrating a joint part according to another modification example.
Figure 16:
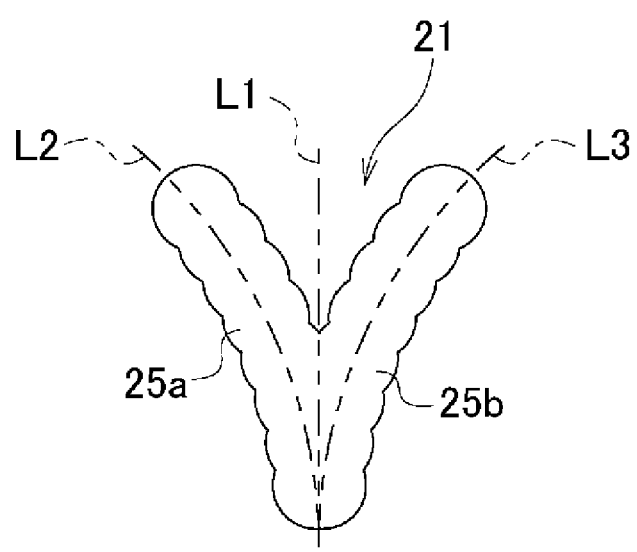
FIG. 16 is a plan view illustrating a joint part according to another modification example.

FIGS. 14 to 16 illustrate modification examples of the shapes of the joint parts 21.

In the modification example of FIG. 14, the welded parts 25a and 25b are separated from each other in the circumferential direction without overlapping each other on the inner circumference 23e side.

In the modification example of FIG. 15, the third line L3 overlaps the first line L1. In accordance with this, the welded part 25b on the other side lies in the radial direction.

In the modification example of FIG. 16, the welded parts 25a and 25b are formed to have curved shapes.

Furthermore, as described above, the shapes of the joint parts 21 can be suitably set in accordance with a difference between the deformation amounts in the inner and outer circumferences 23e and 23f of the wave washer 23. For example, the welded parts 25a and 25b may be provided in dashed line shapes by separating adjacent welding spots 27 from each other. In addition, the opening angle between the welded parts 25a and 25b and the lengths thereof can be changed. Moreover, the shape of only one of the welded parts 25a and 25b can be changed. In addition, the joint parts 21 of the Example 1 are at intervals from with respect to the inner circumference 23e and the outer circumference 23f of the wave washer 23 in a plan view. However, the joint parts 21 can also have shapes lying from the inner circumference 23e to the outer circumference 23f.

The invention claimed is:

1. A flexible member comprising:
a main body part in which a plurality of wave washers having closed ring shapes is stacked in an axial direction and joined to each other by a plurality of joint parts, and the main body part is able to be bent with respect to the axial direction due to elastic deformation of the wave washers,
wherein each of the plurality of joint parts comprises: a pair of welded parts in linear shape, being gradually separated from each other in a circumferential direction from an inner circumferential side toward an outer circumferential side of the wave washer.

2. The flexible member according to claim 1,
wherein in the pair of welded parts, one welded part is provided on a second line extending in a direction intersecting a first line extending in a radiating direction from a center of the wave washer, and the other welded part is provided on a third line extending in a direction intersecting the second line.

3. The flexible member according to claim 1,
wherein each of the pair of welded parts is provided to have a continuously linear shape.

4. The flexible member according to claim 3,
wherein the pair of welded parts has a V-shape in which the welded parts overlap each other on the inner circumferential side in the wave washer.

5. The flexible member according to claim 1,
wherein each of the plurality of wave washers includes a plurality of mountain parts and valley parts between the mountain parts in the circumferential direction, the mountain parts and the valley parts of adjacent wave washers abut each other, and abutment portions of the mountain parts and the valley parts are joined to each other by the joint parts.

6. The flexible member according to claim 2,
wherein each of the pair of welded parts is provided to have a continuously linear shape.

7. The flexible member according to claim 6,
wherein the pair of welded parts has a V-shape in which the welded parts overlap each other on the inner circumferential side in the wave washer.

8. The flexible member according to claim 2,
wherein each of the plurality of wave washers includes a plurality of mountain parts and valley parts between the mountain parts in the circumferential direction, the mountain parts and the valley parts of adjacent wave washers abut each other, and abutment portions of the mountain parts and the valley parts are joined to each other by the joint parts.

9. The flexible member according to claim 3,
wherein each of the plurality of wave washers includes a plurality of mountain parts and valley parts between the mountain parts in the circumferential direction, the mountain parts and the valley parts of adjacent wave washers abut each other, and abutment portions of the mountain parts and the valley parts are joined to each other by the joint parts.

10. The flexible member according to claim 4,
wherein each of the plurality of wave washers includes a plurality of mountain parts and valley parts between the mountain parts in the circumferential direction, the mountain parts and the valley parts of adjacent wave washers abut each other, and abutment portions of the mountain parts and the valley parts are joined to each other by the joint parts.

* * * * *